(12) United States Patent
Lewis

(10) Patent No.: US 6,379,647 B2
(45) Date of Patent: *Apr. 30, 2002

(54) USE OF MONONUCLEAR PHAGOCYTES IN IN VIVO IMAGING OF HYPOXIC/ISCHAEMIC TISSUE

(75) Inventor: Claire Elizabeth Lewis, Sheffield (GB)

(73) Assignee: Oxford Biomedica (UK) Limited, Oxford (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,720
(22) PCT Filed: Mar. 18, 1998
(86) PCT No.: PCT/GB98/00637
§ 371 Date: Nov. 8, 1999
§ 102(e) Date: Nov. 8, 1999
(87) PCT Pub. No.: WO98/57665
PCT Pub. Date: Dec. 23, 1998

(30) Foreign Application Priority Data

Mar. 18, 1997 (GB) .............................. 9705521

(51) Int. Cl.$^7$ ........................ A61K 51/00; A61K 49/00; A61B 5/055
(52) U.S. Cl. .................... 424/1.17; 424/1.49; 424/1.69; 424/9.34; 424/9.6
(58) Field of Search ............................... 424/1.49, 1.41, 424/1.53, 1.69, 9.34, 9.4, 1.45, 145.1, 143.1, 158.1, 179.1, 1.17, 9.6; 530/388.23, 388.24, 388.7, 391.3

(56) References Cited

U.S. PATENT DOCUMENTS

| 5,155,215 A | 10/1992 | Ranney ........................ 534/16 |
| 5,364,612 A | 11/1994 | Goldenberg ................ 424/1.53 |
| 5,387,692 A | * 2/1995 | Riley et al. .............. 548/313.7 |
| 5,422,090 A | * 6/1995 | Stephens et al. ............ 424/1.69 |
| 5,632,968 A | 5/1997 | Goldenberg ................ 424/1.49 |

FOREIGN PATENT DOCUMENTS

| EP | 726 077 A2 | 8/1996 |
| WO | WO 89/10758 | 11/1989 |
| WO | WO 90/01295 | 2/1990 |
| WO | WO 90/10463 | 9/1990 |
| WO | WO/92/01469 | 2/1992 |
| WO | WO 92/17216 | 10/1992 |
| WO | WO 93/10747 | 6/1993 |
| WO | WO 96/34872 | 11/1996 |
| WO | WO 97/31949 | 9/1997 |
| WO | WO 98/15294 | 4/1998 |

OTHER PUBLICATIONS

"ANAWA Conjugation Services. Conjugation Service", http://www.anawa.ch/conj.htm, 1 pg. (Printed Aug. 30, 2001.
"Immunology Protocols: Antibody Labeling", http://www-.protocol-online.net/immuno/antibody/antibody_labeling-.htm, 2 pgs. (Printed Aug. 30, 2001).
O'Sullivan C. and CE Lewis (1994) J. Pathol. 172:229–235.
Kallinowski F. (1996) Cancer J. 9:37–40.
Knighton DR, et al. (1983) Science. 221:1238–85.
Text book, Leek RD, Lewis CE, Whitehouse R and Harris AL. (1996).
Stein I, et al. (1995) Mol. Cell. Biol. 15:5363–68.
Text book, Parums D, In The Macrophage. (1993) CE Lewis and J McGee. Oxford University Press, Oxford.
Krupinski J, et al. (1996) Folia Neuropathologica 34:17–24.
Nordsmark M., Hoyer M., Keller J. And Nielsen OS. (1996). Int. J. Radiation Biology Physics. 35:701–708.
Rasey JS., Koh WJ., Evans ML., Peterson LM., Lewellen TK., Graham MM. And Krohn KA. (1996) Int. J. Radiation Oncology Biology Physics. 36:417–28.
Urtaswn RC., Paliament MB., McEwan AJ., Mercer JR., Mannan RH., Weibe LI., Morin C. and Chapman JD. (1996) British J. Cancer. 74:5209–5212.
Baldwin NJ. and Ng TC. (1996) Magnetic Resonance Imaging. 14:541–551.
Haddala H., et al. (1993) Biochem. Biophys. Res. Common. 195:1174–83.
Mantovani A., et al. (1993) Res. Immunol. 144:280–83.
Martinet N., et al. (1992). Cancer. 70:854–60.
Roone E., et al. (1991). FEBS Letts. 288:233–36.
Gyetko M.R., et al. (1993). J. Leuk. Biol. 53:598–601.
Steven F., et al. (1991). Eur. J. Biochem. 196:431–8.
Zavala F. And Lenfant M. (1987) Annals Acad Sci. 496:240–49.
1996, Leek R D et al., "Association of Macrophage Infiltration with Angiogenesis and Prognosis in Invasive breast Carcinoma", Cancer Research, vol. 56, Oct. 15, 1996, pp. 4625–4629 (XP002056968).
1997, Database WPI, Section Ch, Week 9741, Derwent Publications Ltd., London, GB, Class B04, An 97–448634 XP002086354 & WO 97/31949 A (Pharmacia & Upjohn AB), Sep. 4, 1997.

* cited by examiner

Primary Examiner—Michael G. Hartley
(74) Attorney, Agent, or Firm—Merchant & Gould P.C.

(57) ABSTRACT

The invention relates to the imaging, preferably of hypoxic or ischaemic sites using mononuclear phagocytes. Specifically, the migratory behavior of the mononuclear phagocytes is exploited with a view to targeting imaging agents to sites that mononuclear phagocytes penetrate.

10 Claims, 5 Drawing Sheets

Figure 3 (ii)
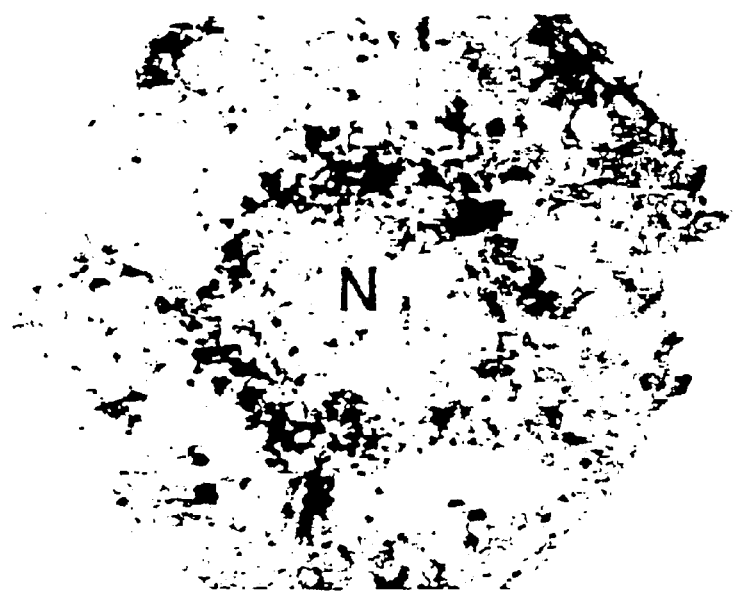

Figure 3 (iii)
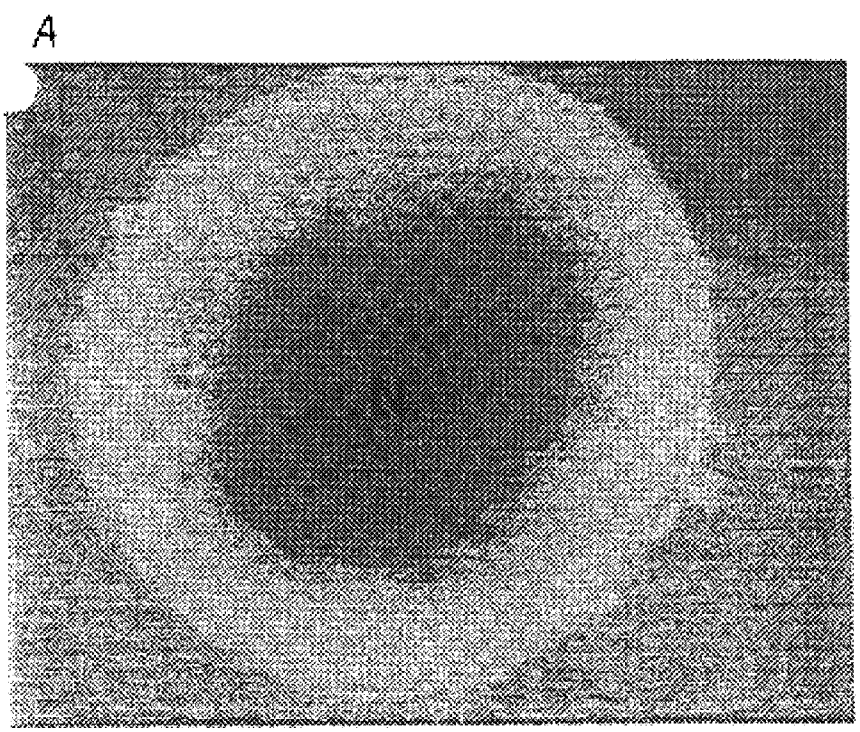
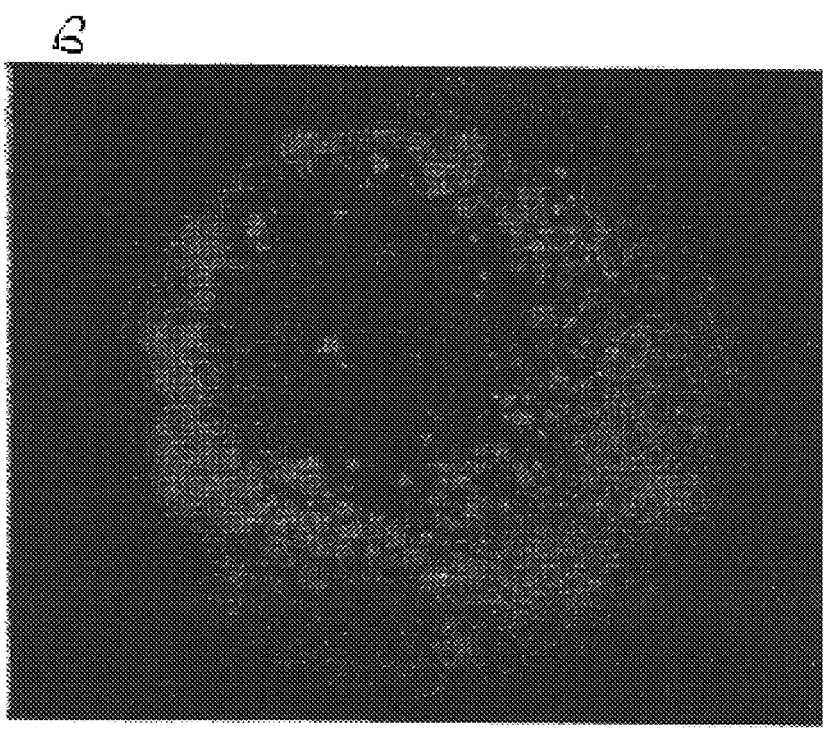

USE OF MONONUCLEAR PHAGOCYTES IN IN VIVO IMAGING OF HYPOXIC/ISCHAEMIC TISSUE

This application is a 371 of PCT/GB98/00637, filed Mar. 18, 1998.

The invention relates to a method of delivering imaging agents; means therefor including components thereof which have particular, but not exclusive, application in the development of therapies for cancer or coronary heart disease.

Macrophages often comprise 20–60% of the tumour cell mass in breast carcinomas and form intimate contacts with malignant cells. This has long been thought to represent part of the host's defence mechanisms against the tumour; however, their function at such sites in the body remains an enigma at present as macrophages isolated from human or murine tumours exhibit reduced tumouricidal, phagocvtic and antigen-presenting activities compared to those from normal tissues (1).

Monocites are produced in the bloodstream and extravasate (i.e. exit) into surrounding tissues including such diseased tissues as malignant tumours and atherosclerotic plaques, where they differentiate into macrophages and perform immune, secretory, phagocytic and other functions. Monocytes and macrophages are collectively termed mononuclear phagocytes. As tissue macrophages have a lifespan of 60 to 90 days and the number of macrophages in tumours remains constant, it is believed that there is a constant attachment of monocytes to the tumour endothelium and influx of monocytes into the tumour cell mass.

Hypoxia, that is, very low levels of oxygen, exist only in some forms of diseased tissue (e.g. malignant tumours, ischaemic heart tissue, retinal tissue etc.) (2). Hypoxia and/or hypoglycaemia is thought to occur in growing tumours when the increasing metabolic demands of the rapidly expanding tumour cell population outstrip the supply of oxygen/glucose etc., made available to them by simple diffusion across the tumour mass from vessels in surrounding normal tissues.

Recent and surprising data indicate that once monocytes enter a tumour from the bloodstream, they rapidly differentiate into macrophages and preferentially congregate in hypoxic (i.e. poorly vascularised and necrotic) sites deep within a tumour mass remote from blood vessels. Refer to FIG. 1, which represents a bar chart of the Distribution of Macrophages in Relation to Blood Vessels. Moreover, breast tumours, with more hypoxic/necrotic areas, are more heavily infiltrated with macrophages, which preferentially locate to, or around, the necrotic sites (refer to FIG. 2, which represents a bar chart of the Association of Macrophage Index with Necrosis in Breast Carcinomas). Experimental hypoxia has been shown to induce the production of angiogenic factors by macrophages in vitro (3). Taken together these data could underpin our recent finding, that increased numbers of macrophages in breast tumours equate with increased fatalities in breast cancer (4).

We have also shown recently that human macrophages accumulate specifically in cell layers immediately adjacent to the central areas of necrosis in three-dimensional cultures of human cancer cells. Many previous studies have shown that this viable rim of tumour cells around the necrotic core of such spheroids are severely hypoxic relative to the outer layers of tumour cells in these cultures (5). That macrophages congregate in hypoxic diseased tissues other than malignant tissue has been shown for coronary heart disease (6), as well as such cerebrovascular disorders of the central nervous system as strokes and cerebral malaria (7).

The observation that tumour and other forms of ischaemic tissue are regions of poor oxygenation has lead to the development of a number of techniques to assess oxygen tension in these tissues. Invasive surgical procedures include the insertion of polarographic micro-electrodes into tumour tissue to measure directly the levels of oxygen in a given tissue (2). Non invasive techniques have also been adopted which involve the use of radiopharmaceuticals (eg F-18 Fluoromisonidazole) which bind to hypoxic cells (8). The concentration of the agents are then detected and quantified by methods such as whole body positron emission tomography (PET imaging) (9). A major problem with this imaging technique is that radiopharmaceuticals tend to be neurotoxic due to their lipid solubility. Clearly this problem would be overcome if it were possible to bind these products to a delivery means. A further major problem with this imaging technique is the poor level of resolution achieved by radiopharmaceuticals due to a relatively high background detection in tissues that do not have appreciable levels of hypoxia. An improvement of the level of detection in hypoxia sites can be achieved if sufficient time is allowed for the clearance of the radiopharmaceutical from non target tissues. However this can take several hours to achieve and is therefore not a desirable situation.

The current state of the art describes a number of means to enhance the localisation of imaging agents to hypoxic and/or ischaemic sites. In broad terms current techniques involve the encapsulation of imaging pharmaceuticals within microvesicles. Alternatively the imaging agents can be directly modified to enable either the localisation of the agent to the desired tissue or enhance their detection when the agent accumulates in the target tissue.

Typically microspheres encapsulating an imaging agent are liposomes composed of either pure phospholipid or a mixture of phospholipid and phosphoglyceride. They are advantageous due to the ease with which the microspheres can be produced containing the imaging pharmaceuticals. By altering conditions during manufacture microspheres can be produced that have diameters of less than 200 NH enables them to be intravenously injected and able to pass through the pulmonary capillary bed. Furthermore the biochemical nature of the liposome confers permeability across blood vessel membranes to access the tumour site or region of ischaemia. Liposomes of this type show high echogenicity both in vitro and in vivo which would be a necessary requirement using techniques of magnetic resonance imaging (11), fluoroscopy and computerised tomography (10).

However this technology does suffer a major disadvantage in that the liposomes lack an intrinsic affinity for the targeted tissue and relies on a local intravenous injection of the liposome composition in the vicinity of the diseased tissue.

What patients require is a rapid and accurate diagnosis of their condition so that an effective treatment regime can be established as quickly and accurately as possible. The development of an effective means of targeting imaging means to hypoxic/ischaemic sites would obviously benefit both clinicians and patients in the diagnosis and treatment of diseases such as cancer and coronary heart disease.

An alternative strategy is to chemically modify an agent that has a natural affinity for tumour/ischaemic tissue to enable the detection of the agent at the targeted tissue.

Monosaccharide derivatives have been used as imaging agents (Patent application no. WO.9634872-A). Glucose levels have been shown to be an important indicator in diagnosis of Alzheimer's disease, Parkinson dementia, epilepsy, diabetes and myocardial ischaemia. The elevated levels of glucose consumption in tumour or ischaemic tissue has been exploited by using iodinated glucose to identify these regions. Although modified monosaccharides have excellent in vivo stability they have a general biodistribution in the body and problems with optimising the signal to noise ratio during treatment can arise.

The labelling of peptides with technetium-99m and there detection via scintigraphic imaging has been used in the diagnosis of tumours (Patent application no. WO.9310747-A). Peptides are typically composed of 4-100 amino acid residues. The technetium-99m labelled peptides have been successful used to diagnose kidney disorders by scintigraphic imaging. However although imaging peptides have excellent in vivo stability they lack an intrinsic targeting property making resolution somewhat problematic.

More recently the use of a radioactive copper complex of dithiosemicarbazone has been employed to image regions of hypoxia and/or mitochondrial dysfunction (EP-726077-A). The composition is advantageous due to improved permeability and retention in target cells but with a short residence in non-targeted cells. The imaging potential of this composition is improved due to the fact that it is only reduced in tissue containing an excess of electrons (eg tissues that contain dysfinctional mitochondria). However although copper containing dithiocarbazone shows retention in hypoxic tissue there are still significant levels of the composition in non-targeted normoxic tissue thus reducing detection resolution.

Finally, the use of monoclonal antibodies to target radioactive and non radioactive imaging agents has been exploited. The expression of specific membrane proteins has lead to the production of monoclonal antibodies to these membrane proteins to enable the targeting of imaging agents to tumour tissue. However this advantage is offset by the poor access of the tagged antibodies to the tumour tissue.

In summary the compositions that have been described either lack an intrinsic means of targeting the imaging agent to a diseased tissue or have poor access to the sites of hypoxia/ischaemia. This leads to a poor signal to noise ratio resulting in reduced imaging resolution.

It is therefore an object of this invention to identify a means to target imaging agents to regions of hypoxia/ischaemia which exploits the fact that mononuclear phagocytes have an affinity for regions of hypoxia/ischaemia.

The invention in its broadest aspect, comprises the use of mononuclear phagocytes to deliver conventional imaging agents to tissues and especially hypoxic/ischaemic sites.

According to a first aspect of the invention there is therefore provided an imaging means comprising an imaging agent attached to an agent that binds to a cell surface element of a mononuclear phagocyte.

The invention comprises the conjugation of imaging agents to the surface of macrophages via macrophage specific cell surface proteins/receptors (eg CD68, CD87, CSF-1). The imaging agent could be attached via a monoclonal antibody, ideally humanised, to one or more of these cell surface proteins or to a ligand specific for a particular macrophage cell surface marker. The macrophages could be modified either in vivo or ex vivo and reintroduced into the patient to allow macrophage migration into the hypoxic/ischaemic tissue. It may be advantageous, but not always necessary, to use an imaging acent that becomes more readily detected due to the conditions of hypoxia or ischaemia.

In a preferred embodiment of the invention said imaging agent is of a conventional nature such as, without limitation, an imaging pharmaceutical such as a radiopharmaceutical or a technetium-99m peptide.

It is therefore a further object to provide a novel imaging means the detection of which is enhanced by hypoxic/ischaemic conditions.

According to a further aspect of the invention there is provided an imaging means comprising a hypoxia enhanced imaging agent and an agent that binds to a cell surface element of a mononuclear phagocyte.

It will therefore be apparent that the hypoxia enhancing imaging agent will be affected by hypoxic conditions and typically affected so as to lead to enhanced detection in such conditions. A typical example of this sort of agent is described in WO 9634872-A. Moreover, said binding agent, which is typically coupled to said imaging agent, attaches the composition to mononuclear phagocytes and so targets the imaging agents, to sites typically infiltrated by mononuclear phagocytes. Thus in the instance where the said mononuclear phagocytes penetrate hypoxic sites said composition is suitably delivered to such sites and the imaging agent shows enhanced detection.

The invention is elegant in so far as the body's own mechanisms are exploited for the specific delivery of the imaging agent to regions of hypoxia or ischaemia.

Given the above nature of the invention agents suitable for use in manufacturing the composition will be known to those skilled in the art and therefore the following preferred embodiments are not intended to be exhaustive but rather illustrative.

It may be preferable to conjugate said imaging agent to a carrier molecule that promotes the internalisation of the imaging composition into mononuclear phagocytes. Intemalisation signals include, but are not limited to, plasminogen activation inhibitors (PAI-1 PAI-2) or protease nexin (PN), which bind to, and cause the internalisation of CD87 (the receptor for Urokinase Plasminogen Activator) into monocytes and macrophages.

In a preferred embodiment of the invention said binding agent is adapted to bind to any one or more cell surface mononuclear phagocyte molecules such as antigens or receptors.

Further, said bindina agent may comprise an antibody to any one or more of said molecules such as antigens or receptors, or an effective fragment of said antibody. Alternatively still said binding agent may comprise a suitable ligand either synthetically manufactured or naturally occurring. For example, chemicals such as benzodiazepines and PK1195 bind to a specifc receptor on the surface of macrophages (Zavala and Lenfant (1987) Annals N Y Acad Sin 496, 240-249).

A brief list of those cell surface molecules that may be targeted by said binding agent is as follows; CD87; the receptor for human Colony Stimulating Factor (CSF-1); CD11b; CD3; the scavenger receptor; all or part of the receptor for the various forms of human monocyte chemoattractant protein (MCP-1,2, etc); CD14; mannose or mannose-6-phosphate surface receptors.

According to yet a further aspect of the invention there is provided a delivery system for targeting imaging compositions to hypoxic or ischaemic sites comprising an imaging agent and, optionally, an agent for controlling the functional effectiveness thereof, and coupled thereto, a binding agent for a cell surface molecule of a mononuclear phagocyte.

According to yet a further aspect of the invention there is provided a method for targeting imaging agents to hypoxic or ischaemic sites comprising;

(i) coupling at least one of said agents to a binding agent of a cell surface molecule expressed by a mononuclear phagocyte;

(ii) exposing said coupled agents to the mononuclear phagocytes; and (iii) allowing the said phagocytes to migrate under conditions that support migration in vivo.

According to yet a further aspect to the invention there is provided a method for imaging hypoxic or ischaemic sites comprising administering to an individual to be treated the imaging means of the invention.

According to yet a further aspect of the invention there is provided mononuclear phagocytes having coupled thereto, or internalised therein, an imaging agent and an agent that is adapted to bind to a mononuclear phagocyte ligand which is typically found on the cell surface of the said mononuclear phagocyte.

In essence the invention describes the use of mononuclear phagocytes to deliver imaging agents to regions of hypoxia/ischaemia to increase the resolution of detection of said imaging agent either through localisation or by use of hypoxia enhanced imaging agent.

BRIEF DESCRIPTION OF THE DRAWINGS

An embodiment of the invention will now be described by way of example only with reference to the following wherein.

Figure 1:
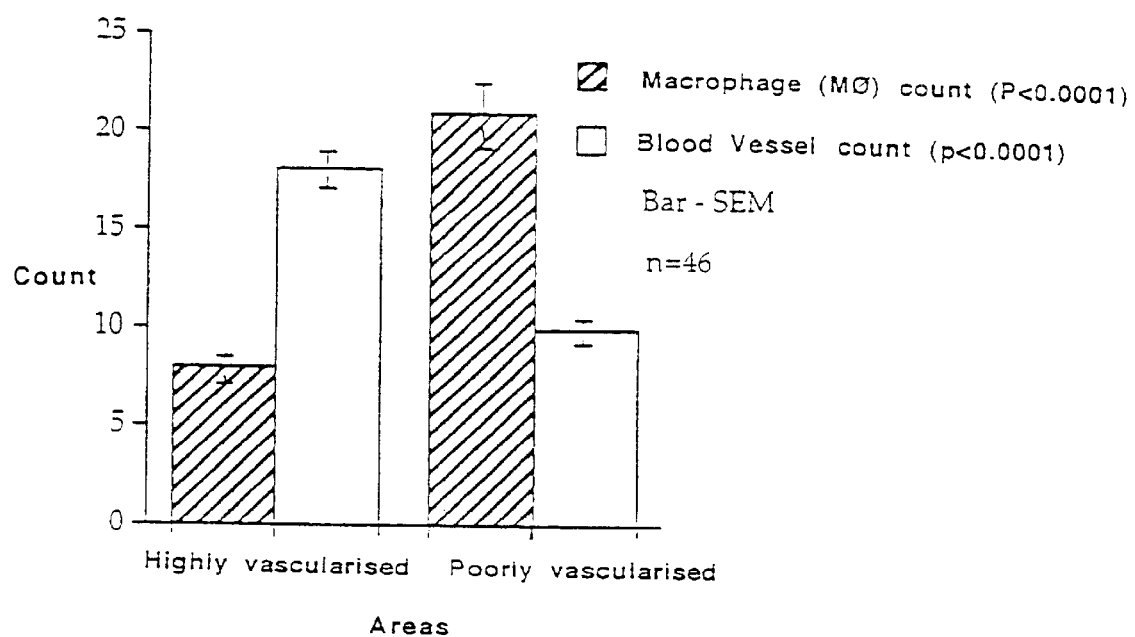
FIG. 1 shows the distribution of macrophages in relation to blood vessels.
Figure 2:
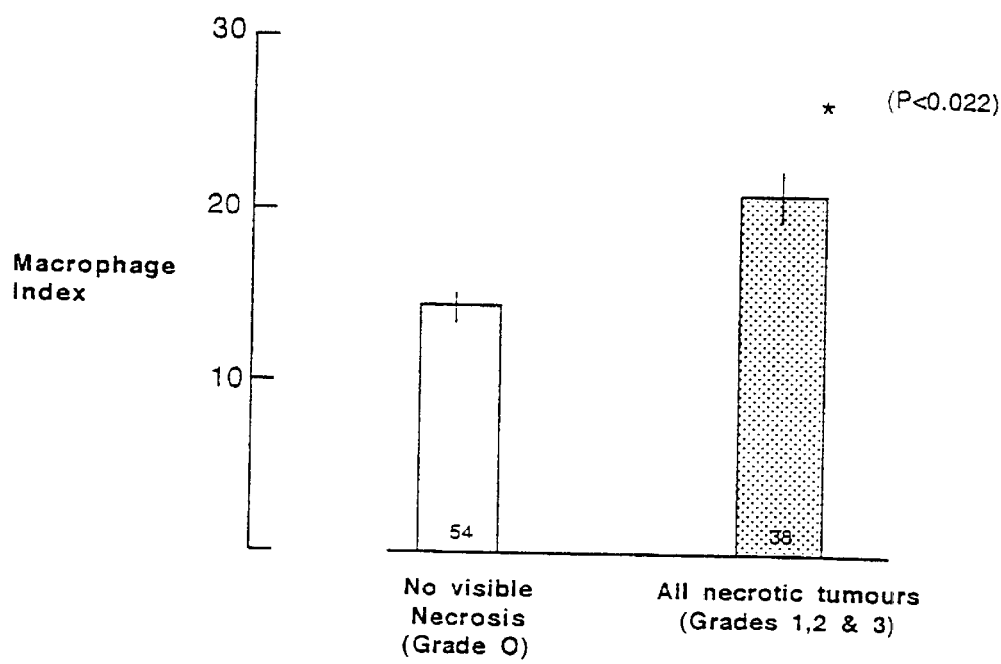
FIG. 2 shows the association of macrophage index with necrosis in breast carcinomas.
Figure 2:
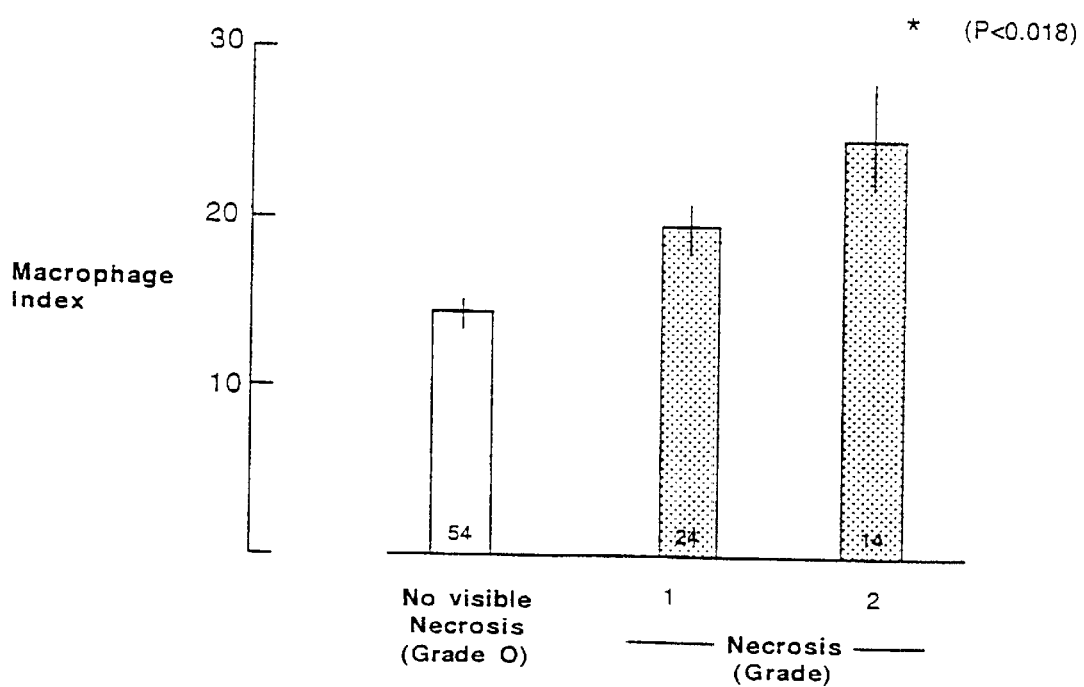

(i) shows the oxygen profile across a tumour cell spheroid. All but the cells in the outer 100 um of these 3-D cultures are hypoxic (i.e. experiencing oxygen levels of 0–15 $pO_2$ mmHg; a level equivalent to that present in hypoxic/necrotic sites in human tumours). This hypoxia is produced by the inability of oxygen to diffuse into the central areas of spheroid. The glucouse profile of the spheriod is similar to that seen for oxygen.

(ii) shows two different tumour spheroids (made of the breast cancer cell line, MCF-7) following co-culture for 24 h with the monocytic cell line, U937. The U937 cells (darkly stained cells labelled with a monoclonal antibody to the pan-macrophage marker, CD68) accumulate in the hypoxic rim of viable, but hypoxic tumour cells around the central areas of necrosis ("N").

(iii) shows the infiltration into tumour spheroids of U937 cells preloaded with fluorescent dye. The top panel is a light micrograph showing the opaque (iv) central area of necrosis ("N") which forms in these spheriods as a consequence of nutrient (e.g. oxygen, glucose etc) deprivation. The bottom panel is the same spheriod using a fluorescent microscope to show the presence within the spheriod of the fluorescent (i.e. light coloured cells) U937 cells. The latter take up a similar position to that seen in (ii), i.e. they congregate in a collar of hypoxic tumour cells around the central areas of necrosis.

MATERIALS AND METHOD

Infiltration of multi-cellular human tumour spheroids with human macrophages (U937 cells or monocytes).

Tumour spheroids were established in culture using the MC7 cell line (ATCC) using the following procedure.

A. Establishment of Spheroid Cultures

1. Uniformly sized spheroids were grown in standard 96-well tissue culture plates.

2. A 1.5% solution of agarose was prepared in media and autoclaved (the medial should not contain any supplements or fetal calf serum as this causes the formation of bubbles and the cells will plate down and not form spheriods).

3. 100 $\mu l$ of the agarose was aliquoted into each well and allowed to cool. Plates were then warmed to 37° C. before use.

4. Monolayers of tumour cell lines were stripped in the exponential growth phase, resuspended and counted using a haemocytometer.

The cells were then diluted to the appropriate number of cells for spheroid initiation. For T47D and HT29 this was 1000 cells per well and for MCF-7 it was 2000 cells per well. Each well was filed with 200 $\mu l$ of the cell suspension. The final concentration of the cell suspension for T47D was 5000 cells per ml. (NB spheriods were grown in the media used normally for each of the cell lines (eg T47D are grown in DMEM supplemented with antiobiotics and fungicides).

5. Following initiation, the spheroids were incubated at 37° C. in a $CO_2$ incubator and left undisturbed for 5 days to allow aggregation to occur.

6. Spheroids were fed fresh medium three times per week.

B. Co-culture of spheroids with macrophages

1. Moncytic cell lines eg U937 cells), peripheral blood moncytes or moncyte-derived macrophages were introduced into the spheroid once the spheroids have formed necrotic centres. This stage depends upon the cell line used. For MCF-7 and T47D it was after 2–3 weeks of culture, when a dark area can be seen in the centre of the spheroid.

2. This was done by removing 100 $\mu l$ of media from the wells and replacing it with a suspension of macrophages (50,000 per well). For cell lines, the change in media was not a problem but for PMBC the media should be serially changed for both the spheroid and the macrophage until they are in the same media. These cells infiltrated the spheroids in the first hour of co-culture and continued to do so for up to 48 hrs. After this, the spheroids were removed from the wells using a glass of Pasteur pipette, placed in a test tube and rinsed in PBS to remove any loose macrophages or cell debris.

3. The spheroids were then allowed to settle to the bottom of the tube, the PBS removed and the spheroids processed for paraffin embedding (or frozen in OCT).

Figure 3:
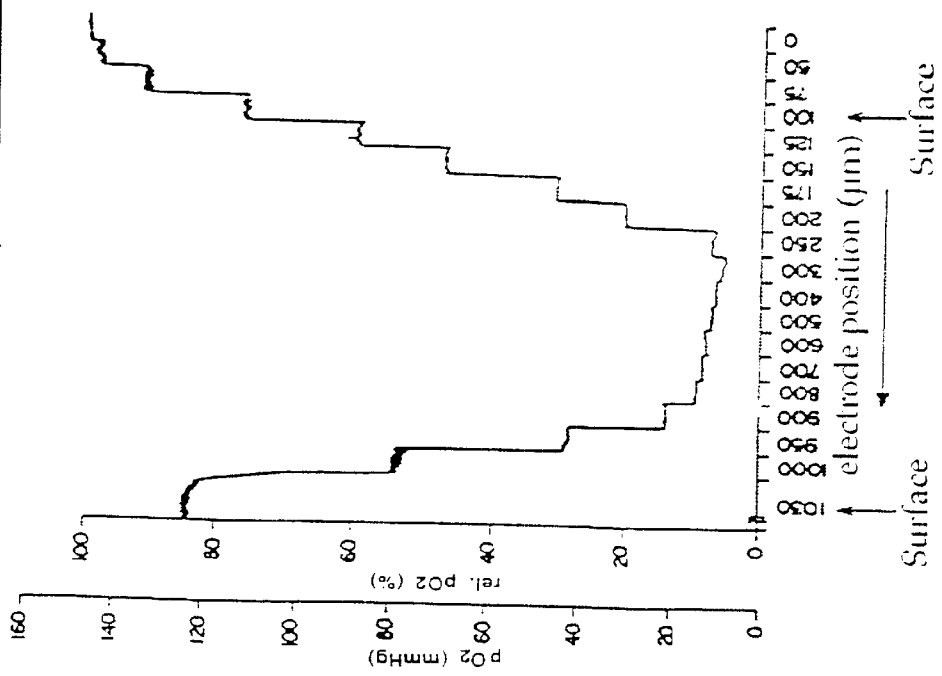
FIG. 3 shows macrophage infiltration into hypoxic areas in tumour spheroids (i.e. an in vitro model of tumour hypoxia imaging)

The results of an experiment showing infiltration of MCF-7 spheroids with U937 cells is shown in FIG. 3. Each spheroid displays the typical central area of necrosis ('N') surrounded by a collar of hypoxic tumour cells (approx 5–10 cells in thickness) and then several outer layers of cells that are relatively normoxic. U937 cells, immuno-labelled (dark staining) for the pan macrophage marker CD68, can be seem accummulating in the hypoxic tumour cell layers around the central necrosis.

Demonstration of Infiltration into Spheroids of Monocytic Cells Labelled with a Fluorescent Dye.

U937 cells were incubated with 90 $\mu l$ of 4-(4-(didecylamino)styryl)-N-methyl pyridinium iodide (2 mg/ml in abs ethanol) for 45 minutes then washed to remove the excess dye. Multicell spheroids (5–600 $\mu m$ in diameter) were placed in a bacterial petri dish (agarose would flouresce and they would adhere to tissue culture plastic) and incubated with 75000 dye-loaded U937 cells per spheroid. The final volume was 15 mls. After 4 days of co-culture spheroids were washed to remove unattached macrophages and photographed using a fluorescence microscope.

The result is shown in FIG. 3(iii). Panel A in FIG. 3(iii) shows a section through a spheroid photographed under white light. The central necrotic core (N) is visible as a dark area. Panel B, photographed under fluorescence optics, shows accummulation of macrophages labelled with fluorescent dye, in the hypoxic region around the necrotic core.

C. Paraffin embedding of spheroids
1. Spheroids were immersed in formalin for 2 hours or overnight.
2. They were then either embedded in agar and processed or placed in a piece of pre-folded tissue paper which was then folded and placed in a tissue-processing cassette. Alternatively a Cellsafe biopsy cassette was used (a mesh chamber in which the spheroids are placed). The cassette was then closed and placed inside the processing cassette. The mesh prevented the spheroids escaping.
3. The spheroid preparations were processed through ascending grades of alcohol to paraffin wax using a Citadel 2000 Histopathology Processing Unit.
4. Sections of the paraffin wax blocks were cut using a microtome onto coated sides.

D. Immunohistochemistry for CD68 (a pan macrophage marker) to localise macrophages in spheroids
1. Spheroid sections were dewaxed in xylene and absolute alcohol.
2. The endogenous peroxidase in the sections was then blocked with 2% H202 in methanol for 10 mins.
3. Antigen retrieval: sections were exposed to proteinases type XXIV for 15 mins at 37° C.

The sections were then incubated in the following: (with 3×5 min washes between each step).
4. Normal serum for 30 mins at room temperature.
5. Primary anti-CD68 monoclonal antisera at a dilution of 1:100 for one hour at room temperature or overnight at 4° C.
6. Secondary antibody (biotinylated horse anti-mouse IgG) for 30 mins at room temperature followed by an avidin-biotin peroxidase complex for 30 minutes at room temperature (ie using the Vector ABC Elite kit).
7. Visualised with the chromagen, DAB or AEC for 20 10 mins.
8. The nuclei were then counterstained with haematoxylin and sections mounted with coverslips for viewing.

NB: Spheroid sections needed to be washed thoroughly in diluent between each steep of the staining protocol to limit background/non-specific staining.

Imaging Agent Delivery

The imaging agent conjugate of choice can be infused (repeatedly or as a single injection) into the general circulation so as to bind in vivo to the surface of systemic mononuclear phagocytes and/or macrophages already resident in diseased tissues (e.g. malignant tumours). Alternatively the imaging agent conjugate can be exposed to monocytes ex vivo, following their purification from the blood of patients using such standard methods such as Ficoll-Hypaque gradients and elutriation as described previously in (12). This method is as follows:
1. Ontain a fresh sample of venous blood in EDTA vacutainer tubes. 15 ml will yield approximately 1 million monocytes.
2. Dilute 1:1 with HBSS and overlay into an equal volume of Ficoll-Paque. (6×12 ml centrifuge tubes are recommended).
3. Centrifuge at 600 g for 15 minutes.
4. Remove plasma layer and carefully remove band of buffy coat cells. Resuspend cells in HBSS.
5. To remove cell clumps pass cell suspension through 30 micron filter.
6. Wash cells by centrifuging at 300 g for 5 minutes and completely removing supernatant, then resuspend in 80 microlitres buffer per 10 million cells. Buffer=PBS supplemented with 2 mM EDTA and 0.5% BAS— degassed.

Homing of blood monocytes loaded up with imaging agent conjugates into malignant tumours can be augmented by prior treatment with conventional systemic therapies which induce local inflammation/necrosis in the diseased tissue (e.g. radiotherapy or chemotherapy in the case of cancer patients). This stimulates the release of chemoattractant factors for monocytes/macrophages such as MCP-1 (13, 14) and would thus enhance the delivery and hence the imaging of the conjugate at the diseased site.

Mode of Production of Selected Imaging Agent Conjugates

EXAMPLE 1

Imaging Agent Conjugated to F(ab)$_2$ of a Monoclonal Antibody to CD87 (uPAR)

This conjugate uses a highly specific F(ab)$_2$ fragment, a monoclonal antibody to CD87 (urokinase plasminogen activator receptor; uPAR), to target naturally occurring uPAR on the surface of monocytes and macrophages.

A monoclonal antibody to CD87 is made as described in (15) and then cleaved/purified to a specific F(ab)$_2$ monoclonal antibody fragment using standard proteolytic methods. Depending upon the part of uPAR used to raise the antibody (i.e. as the antigen), the epitope for the antibody generated may either be in the (i) ligand (i.e. uPA)-binding portion of the uPAR (in which case the imaging agent conjugate will only bind to unoccupied uPAR on monocytes/macrophages), or (ii) the non ligand (i.e. uPA)-binding portion of the uPAR (in which case the imaging agent conjugate will bind to both occupied and unoccupied uPAR on monocytes/macrophages). The most effective imaging agent uptake is likely to be achieved using the latter form of conjugate.

EXAMPLE 2

Imaging Agent Conjugated to PAI-2

This conjugate uses the affinity of plasminogen activator inhibitor 2 (PAI-2) for urokinase plasminogen activator receptor (uPAR)-urokinase plasminogen activator complexes to target the imaging agent to the surface of monocytes and macrophages. PAI-2 triggers the internalization of uPAR-uPA complexes, so the internalization by these cells of the imaging agent attached to PAI-2 is assured.

Naturally occurring PAI-2 is obtained from the culture supernatant of human blood monocytes stimulated maximally with interleukin 1 or 2 as described in (16). This is then purified to homogeneity in the usual manner by elution from an anti-PAI-2 immunoaffinity column. Alternatively, PAI-2 can be produced in a recombinant expression system and purified according to the method of (17).

EXAMPLE 3

Imaging Agent Conjugated to CD14 Micro-Beads

The conjugate comprises an antibody that is specific for the macrophage surface molecule CD14. The antibody is conjugated to magnetic microbeads and applied to monocytes as follows:

1. Add 20 microlitres of CD14 microbeads per 10 million cells, mix and incubate for 15 minutes at 6–12 degrees C.
2. Wash cells by adding 10–20×the labelling volume of buffer and centrifuge at 300 g for 10 minutes, remove supernatant and resuspend in 500 microlitres of buffer per 100 million cells.
3. Choose correct column type (MS+for 10 million total cells, VS+ for 100 million total cells for positive selection) and place in the magnet on the MiniMacs stand.
4. Prepare column by flushing by 500 microlitres of buffer.
5. Apply cell suspension and rinse with 3×500 microlitres of buffer.
6. Remove column from separator, place column on a suitable collection tube, pipette on 1 ml of buffer and flush out the positive cells using the plunger provided.
7. Spheroids grown using the liquid overlay culture technique in 96 well plates were allowed to reach maximal size of approximately 800 microns.
8. Remove approximately 100 microlitres of media from each well of the plate and replace with the labelled monocyte suspension (50,000 cells per ml to give 5,000 cells per spheroid).
9. Allow monocytes to infiltrate overnight.
10. Retrieve spheroids from 96 well plate and wash twice in PBS to remove loosely attached monocytes.
11. Fix in 10% buffered formalin.

To detect the infiltrating monocytes the spheroids are analysed by magnetic resonance imaging (MRI).

These examples are represented as exemplary imaging agent conjugate candidates. It will be understood by those skilled in the art that such conjugates represent selected examples and are not intended to limit the scope of the invention.

The invention hereinbefore described therefore represents a most elegant and effective means and method of delivering an imaging agent to a hypoxic or ischaemic site by use of monocytes and/or macrophages and their natural ability to congregate at a hypoxic or ischaemic site.

REFERENCES

1. O'Sullivan C and Lewis C E (1994) J. Pathol. 172: 229–235.
2. Kallinowski F. (1996) Cancer J. 9: 37–40.
3. Knighton DR, et al. (1983) Science. 221: 1238–85
4. Leek R D, Lewis C E, Whitehouse R and Harris A L. (1996)
5. Stein I, et al. (1995) Mol. Cell. Biol. 15: 5363–68
6. Parums D, In The Macrophage. (1993) C E Lewis and J McGee. Oxford University Press, Oxford.
7. Krupinski J, et al. (1996) Folia Neuropathologica 34: 17–24.
8. Nordsmark M., Hoyer M., Keller J. and Nielsen O S. (1996). Int. J. Radiation Oncology Biology Physics. 35: 701–708.
9. Rasey J S., Koh W J., Evans M L., Peterson L M., Lewellen T K., Graham M M. and Krohn K A. (1996) Int. J. Radiation Oncology Biology Physics. 36: 47–28.
10. Urtaswn R C., Paliament M B., McEwan A J., Mercer J R., Mannan R H., Weibe L I., Morin C. and Chapman J D. (1996) British J. Cancer. 74: 5209–5212.
11. Baldwin N J. and Ng T C. (1996) Magnetic Resonance Imaging. 14: 541–551.
12. Haddala H., et al. (1993) Biochem. Biophys. Res. Common. 195: 1174–83
13. Mantovani A., et al. (1993). Res. Immunol. 144: 280–83.
14. Martinet N., et al. (1992). Cancer. 70: 854–60.
15. Ronne E., et al. (1991). FEBS Letts. 288:233–36.
16. Gyetko M. R., et al. (1993). J. Leuk. Biol. 53: 598–601.
17. Steven F., et al. (1991). Eur. J Biochem. 196: 431–8.
18. Zavala F. and Lenfant M. (1987) Annals Acad Sin. 496: 240–49

I claim:

1. An imaging means comprising:
   i. an imaging agent attached to an agent that binds to a cell surface element of a mononuclear phagocyte;
   ii. a carrier molecule conjugated to the imaging agent; and
   iii. a mononuclear phagocyte that has internalized therein the imaging agent; such that the carrier molecule promotes the internalization of the imaging agent into the mononuclear phagocyte.

2. An imaging means according to claim 1 wherein said cell surface element is a protein.

3. An imaging means according to claim 1 wherein said agent that binds to a cell surface molecule element of a mononuclear phagocyte is an antibody.

4. An imaging means according to claim 3 wherein said antibody is monoclonal.

5. An imaging means according to claims 3 wherein said antibody is humanised.

6. An imaging means according claim 1 wherein said carrier molecule includes PAI-1 or PAI-2 or protease nexin.

7. A method for targeting imaging agents to hypoxic or ischaemic sites comprising:
   i. providing an imaging agent conjugated to a carrier molecule;
   ii. attaching the imaging agent conjugated to said carrier molecule to an agent that binds to the cell surface of a mononuclear phagocyte;
   iii. exposing a mononuclear phagocyte to the imaging agent attached to the binding agent therein; and
   iv. allowing said mononuclear phagocytes to migrate under conditions that support migration in vivo.

8. A method for imaging an hypoxic or ischaemic site in an individual comprising:
   i. administering to the individual an imaging means according to claim 1;
   ii. scanning the individual for the imaging agent; and
   iii. obtaining an image of the hypoxic or ischaemic sites in the individual.

9. Mononuclear phagocytes having internalized therein:
   i. an imaging agent wherein the imaging agent is conjugated to a carrier molecule;
   ii. the imaging agent is attached to an agent that binds to a cell surface element of a mononuclear phagocyte and wherein the carrier molecule promotes the internalization of the imaging agent into the mononuclear phagocyte.

10. A method for targeting imaging agents to hypoxic or ischaemic sites comprising;
   i. providing an imaging agent conjugated to a carrier molecule;
   ii. attaching the imaging agent conjugated to said carrier molecule to an agent that binds to the cell surface of a mononuclear phagocyte;
   iii. exposing a mononuclear phagocyte to the imaging agent attached to the binding agent and internalizing said imaging agent attached to the binding agent therein; and
   iv. allowing said mononuclear phagocyte to migrate under the conditions that support migration in vivo.

* * * * *